Figure 1:
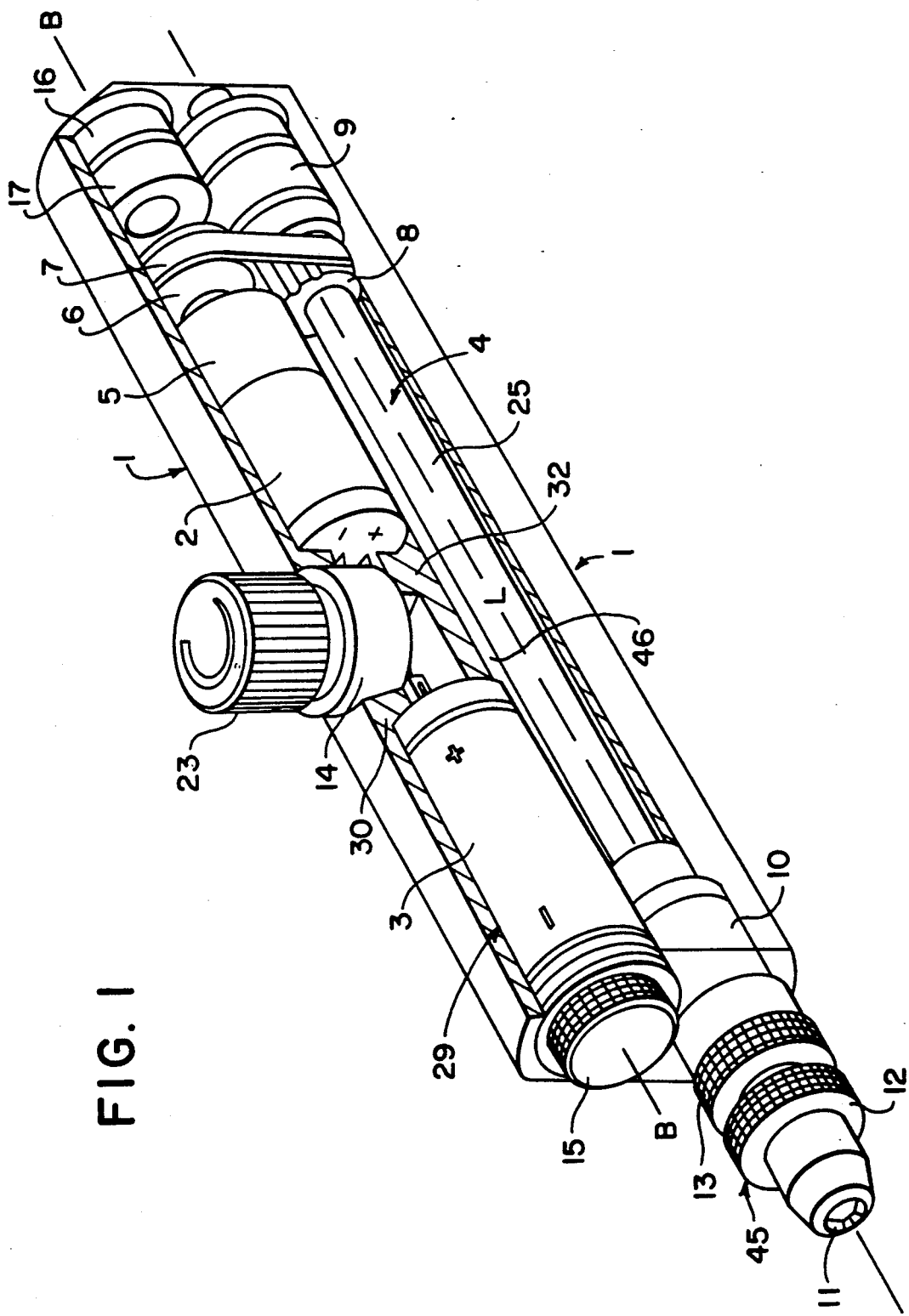

United States Patent [19]

Höcherl et al.

[11] Patent Number: 5,201,750
[45] Date of Patent: Apr. 13, 1993

[54] DILATION CATHETER WITH MOTOR DRIVE FOR DILATION OF BLOOD VESSELS

[75] Inventors: Manfred Höcherl, Rheinfelden; Jörg Reinhardt, Grenzach-Wyhlen, both of Fed. Rep. of Germany

[73] Assignee: VascoMed Institut fur Kathetertechnologie gmbH, Weil am Rhein, Fed. Rep. of Germany

[21] Appl. No.: 572,874

[22] Filed: Aug. 24, 1990

[30] Foreign Application Priority Data

Sep. 6, 1989 [DE] Fed. Rep. of Germany ....... 3929575

[51] Int. Cl.5 .............................................. A61B 17/32
[52] U.S. Cl. ................................... 606/180; 128/755;
604/22; 606/159; 606/170; 606/194
[58] Field of Search ............... 606/180, 108, 159, 104;
604/109, 22, 80, 81, 170; 408/79, 80; 433/101,
29, 115, 165; 81/473

[56] References Cited

U.S. PATENT DOCUMENTS

| | | | |
|---|---|---|---|
| 3,173,417 | 3/1965 | Horner | 606/180 |
| 3,680,642 | 8/1972 | Kirn et al. | 173/13 |
| 3,693,728 | 9/1972 | Stroezel | 173/13 |
| 3,709,630 | 1/1973 | Pohl et al. | 606/180 |
| 3,712,386 | 1/1973 | Peters | 606/180 |
| 3,809,168 | 5/1974 | Fromm | 173/13 |
| 3,842,632 | 10/1974 | Nelson | 433/165 |
| 3,867,943 | 2/1975 | Nordin | 606/180 |
| 3,998,278 | 12/1976 | Stiltz et al. | 173/13 |
| 4,091,880 | 5/1978 | Troutner et al. | 606/104 |
| 4,484,893 | 11/1984 | Finn | 433/29 |
| 4,679,557 | 7/1987 | Opie et al. | 128/305 |
| 4,712,456 | 12/1987 | Yuan | 81/473 |
| 4,756,216 | 7/1988 | Lo | 81/473 |
| 4,823,885 | 4/1989 | Okumura | 81/473 |
| 4,901,610 | 2/1990 | Larson et al. | 81/473 |
| 5,002,553 | 3/1991 | Shiber | 606/159 |
| 5,074,788 | 12/1991 | Nakanishi | 433/115 |

Primary Examiner—C. Fred Rosenbaum
Assistant Examiner—Manuel Mendez
Attorney, Agent, or Firm—Andersono Kill Olick & Oshinsky

[57] ABSTRACT

A dilation catheter for reopening blood vessels includes an electrical motor drive and is insertable through vessels leading to a constriction point and has a working head for widening the vessel constriction. Catheters rotating slowly with up to 500 rpms are known, which because of the geometry of their head crowd soft material blocking vessels towards the sides. The present dilation catheter with motor drive is distinguished by an electric, battery-powered motor with motor gear box, by a spindle supported in a front bearing package with seal and a rear bearing package with seal, a junction point for the dilation catheter is located one end of the spindle, force is transmitted from the motor to the spindle, and a metal housing holding the spindle, motor and battery is shaped for gripping, holding and handling by a half-closed hand of a surgeon between the row of fingers and the thumb. The housing is kept gas-tight up to 130° C. and three bars of pressure by seals in the front and rear bearing packages.

13 Claims, 3 Drawing Sheets

DILATION CATHETER WITH MOTOR DRIVE FOR DILATION OF BLOOD VESSELS

The invention is directed to a dilation catheter for dilating and/or opening of blood vessels with electrical motor drive, wherein the dilation catheter is insertable through vessels directed to a constriction point and has a working head for widening or dilating the vessel constriction.

A plurality of methods of operating with rotating catheters for opening and widening of blood vessels are known. There exist rapidly rotating catheters with rpms between 20,000 per minute and 150,000 per minute, which open a channel in the vessel by milling with a head similar to a milling cutter or which work with methods involving cutting.

Furthermore slowly rotating catheters are known which because of their head geometry crowd vessel blocking materials towards the sides. Several of these motor drives being throwaway products are only to be used once, in others the catheter is a throwaway product and the motor drive can be used again.

Disadvantages are found in the reusable drive units. Since one is obliged to always operate under sterile conditions when vessels are open, the catheter and the motor drive are sterilized. The reusable motor drives tolerate because of their conception, properties and materials only a sterilization with an ethylene oxide gas at low temperatures up to 50° C. and at low pressures lower than 1 bar, so that the systems in the sterilization process are not destroyed. This sterilization method has the disadvantage because of its toxicity, that the items to be sterilized require aeration or ventilation periods of several days, until they can again be used on a patient.

The invention is now based upon the task to create a dilation catheter with motor drive, which can be sterilized in an autoclave and thus can again be reused after a short time.

This task is solved in the invention with a motor drive and a dilation catheter by a combination of the following features:

A. am electrical battery-driven motor including motor gearing,
B. a spindle supported in a front bearing package with seal and rear bearing package with seal,
C. a junction point for the dilation catheter at one end of the spindle,
D. a force transmittal from the motor to the spindle,
E1. a metal housing shaped for gripping and holding as well as handling by means of a half-closed hand between the row of fingers and the thumb of the surgeon; and
E2. a housing which is gas-tight by means of seals for the front and rear bearing package up to at least 130° C. and 3 bars of pressure.

A sterilization of drive systems in autoclaves is presently only possible with large and heavy drives used in bone surgery, which however because of their weight, their size and their conception cannot be utilized in angioplasty.

During autoclaving there occurs sterilization due to high temperatures of approximately 130° C., high pressure of approximately 3 bars and absolute humidity over period of 20 to 40 minutes.

Since this method uses no toxic sterilization gas, no aeration is required, contrary to the sterilization with ethylene oxide gas, and products sterilized in this manner can after a short cooling phase be used again in sterilized environments.

The easy and simple handling of the motor drive due to its geometric layout is achieved by having the housing comprise a battery compartment for the battery with a battery compartment cover, by the motor and the motor gearing being round, while having approximately the same diameter and being aligned in their longitudinal axis parallel to the spindle axis of the spindle, by the motor being switchable on and off by means of an adjustment button arranged between the battery and the motor and by the rpm of the motor being adjustable by means of the electronic motor control through an adjustment button arranged between the battery and the motor.

An easy and rapid replacement of the dilation catheter is attained by inserting the same at the junction point into a chuck with a union nut and a retaining ring.

The introduction of an endoscope, a guide wire, a contrast agent and a laser light conductor through the dilation catheter to the catheter tip is made possible by the dilation catheter and the spindle being hollow and by being able to pass the dilation catheter through the inner lumen of the spindle.

The functional mode of the motor drive is assured by utilizing a toothed belt from the gear wheel fastened on the motor to the toothed sleeve fastened on the spindle by way of a positively defined force transmission.

Furthermore the functional mode of the motor drive is assured and additionally the force acting from the motor on the spindle can be limited by the circumstance that a V-belt serves as a positively locked force transmission from the V-belt pulley fastened at the motor to the V-belt sleeve fastened on the spindle.

The bearing packages are designed inventively in such a way, that the front bearing package consists of a front sleeve, in which the front bearing and an annular support with front bearing- seal are installed, that the rear bearing package consists of a rear bearing and a rear sleeve, that the bearing packages are arranged in the spindle channel of the housing so as to be gas-tight by means of sleeve-type seals, that the front and rear bearings are ball bearings, and that the spindle is embraced by spindle seals which rest on the inside of the sleeves.

Particular attention must be paid to the special seal between the spindle and the bearing blocks. These must be gas-tight, their material must be resistant to sterilization at high pressure and high temperature while in spite of this assuring a smooth drive of the spindle by the motor. This is achieved in the invention by making the spindle seals out of silicone, and by providing the spindle seals with at least one sealing lip.

The housing is made gas tight by using O-rings for the battery compartment seal, the control part seal, the cover seal and the front bearing seal and the sleeve seal.

The advantages achieved in the invention are especially seen in that because of the properties, design and conception a sterilization of the motor drive and the dilation catheter is possible by autoclaving, a time-consuming sterilization with ethylene oxide gas is superfluous and thus a rapid repeat-availability of the drive is afforded. The quantity of the motor drives and dilation catheters which must be procured is reduced or the use of throwaway products is unnecessary. This results in considerable cost savings.

Other features, details and particularities of the invention can be discerned from the embodiment example which is shown in the drawing and explained in the following with particularity.

Figure 2:
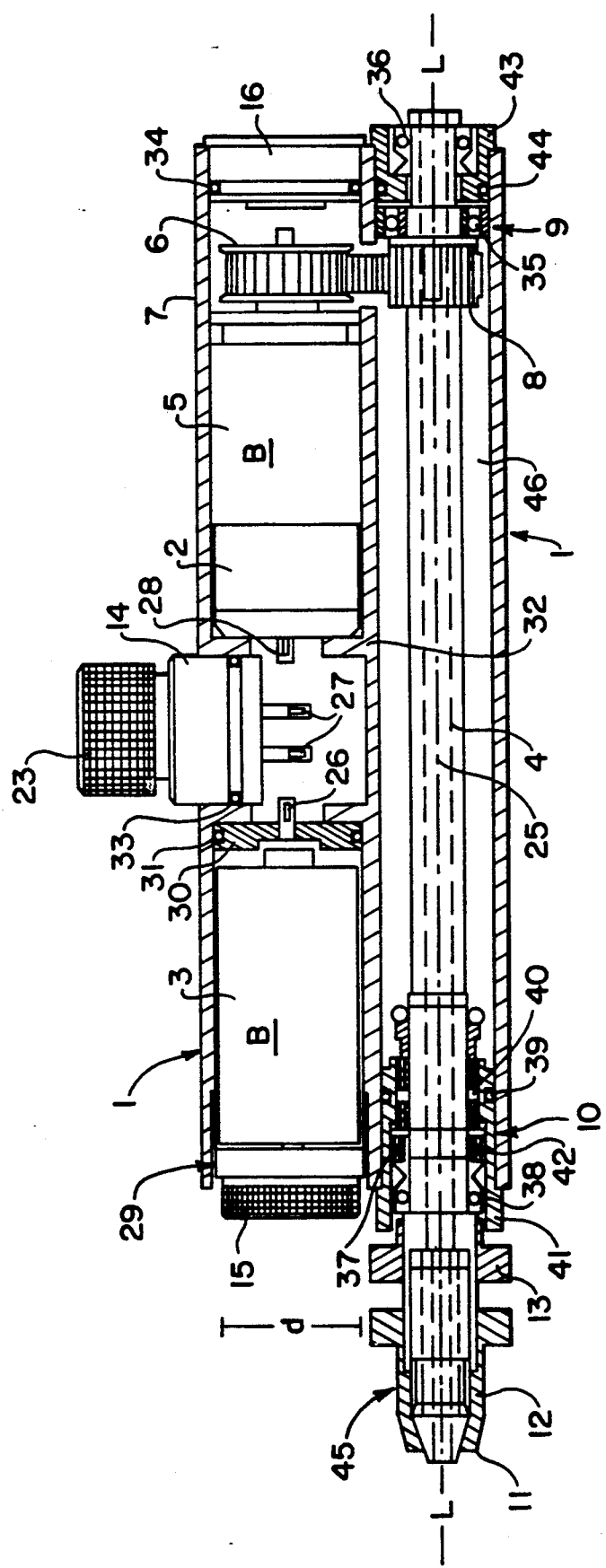
Figure 3:
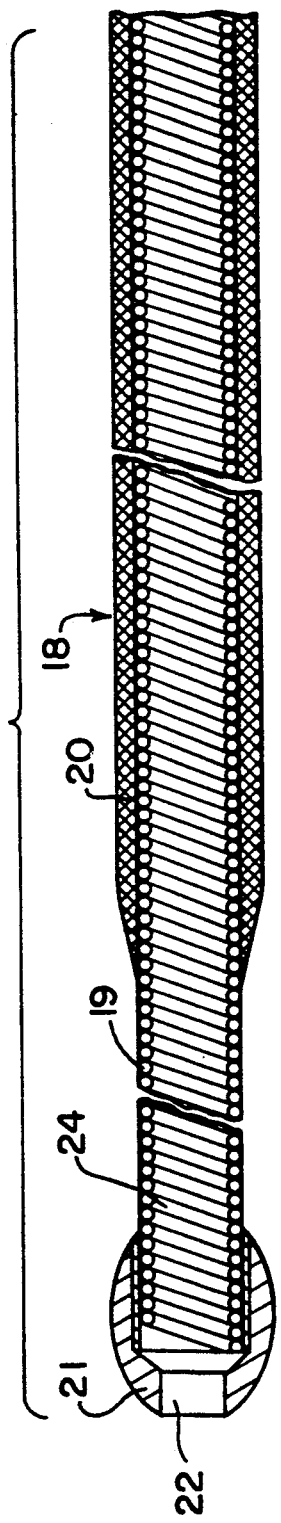

It is shown on:

FIG. 1 a motor drive in perspective view and in section,

FIG. 2 a motor drive viewed from the side in section,

FIG. 3 a dilation catheter in section.

A basically simplified working mode is possible in the reopening of vessels with the use of this motor drive and the dilation catheter 18. Because of the properties, design and conception a sterilization by autoclaving and thus a rapid reavailability of the drive is assured.

For the reopening of vessels the dilation catheter 18 is introduced into the vessel by means of an insertion instrument and is pushed in front of the vessel closure. Subsequently the chuck 11 of the motor drive is slid over the dilation catheter 18 and clamped by means of the union nut 12. The dilation catheter 18 is rotated by the motor drive with up to 500 revolutions per minute, wherein the static friction at the vessel wall which occurs during displacement of a non-rotating catheter is minimized. Because of the flexibility of the dilation catheter 18 and its rotary motion it finds the optimum path through the blocked vessel.

Because of the ellipsoidal geometry of the working head 21 of the dilation catheter 18 the vessel blocking material is crowded towards the side and a channel is formed, whose lumen can be opened further by conventional methods. Since the dilation catheter 18 can be conducted with its other end through the inner lumen 25 of the spindle 4, the user is able to introduce contrast agents, solutions or similar substances by suitable adapters through the catheter inner lumen 24 of the dilation catheter 18 or to manipulate the dilation catheter 18 during the rotation in its direction by means of an inserted guide wire, now shown. The dilation catheter 18 is constructed out of a quadruple spiral 19 and teflon insulation 20. An oval, metallic working head 21 with a distal aperture 22 is arranged upon the quadrupal spiral 19.

The motor drive gear unit driven by a motor 2 is installed in a housing 1. The motor 2 drives the gear wheel 6 by means of the motor drive gear unit 5, which wheel rotates the spindle 4 through a toothed belt 7 and toothed sleeve 8. Overheating of the motor drive gear unit 5 is measured by a temperature sensor 17 built into the drive gear cover 16. The motor 2 is supplied with energy by the battery 3 and can be switched on and off by an adjustment button 23. The adjustment button 23 can also be used for regulating and adjusting the electronic motor control 14 of the motor 4. The motor 5, the battery 3 and the electronic motor control 14 are electrically connected by not shown electric cables joining the battery solder terminals 26, the regulator solder terminals 27 and the motor solder terminals 28. The battery 3 is located in the battery compartment 29 formed by the housing 1, an intermediate wall 32, the battery compartment cover 15 and an inner wall 30. The battery compartment seal 31 of the battery compartment 29, the control part seal 33 of the electronic motor control 14 and the cover seal 34 of the gear unit cover 16 are constructed as 0-rings. The spindle 4 open on both sides is supported in the front bearing package 10 and a rear bearing package 9.

The spindle 4 open on both sides is fitted into the front bearing package 10 and the rear bearing package 9.

The bearing packages 9, 10 seal the housing 1 by means of special seals from silicone also during the sterilization process. The front bearing package 10 consists of a front sleeve 41 which is seated with the front sleeve seal 39 in the spindle channel 46 of the housing 1, and embraces its annular support 37 with the front bearing seal 42 and the front bearing 40, which is a ball bearing. The front spindle seal 38 which is designed as a lip seal, embraces the spindle 4 and seals the front bearing 40 and the spindle channel 46. The front bearing seal 42 and the front sleeve seal 39 are O-rings.

The rear bearing package 9 consists of a rear bearing 35 which is installed in the spindle channel 46, and the rear sleeve 43, which rests with the rear sleeve seal 44 in the spindle channel 46 in a gas-tight manner. A rear spindle seal 36 embracing the spindle 4 with a sealing lip rests on the inside at the rear sleeve 43. The rear sleeve seal 44 is designed as an O-ring.

The bearing packages 9, 10 are located in the spindle channel 46 and are prevented from sliding into same by a step-like widening.

The longitudinal axis B of the round battery 3 and the round motor 2 lie parallel to the spindle axis L of the spindle 4. The electronic motor control 14 with the adjustment button 23 is arranged between the battery 3 which has a diameter d and the motor 2 having approximately the same diameter d. Parallel to the spindle axis L and the longitudinal axis B of motor and battery an intermediate wall 32 is arranged, which divides the motor drive viewed from the side into the spindle channel 46 and the electrical unit consisting of battery 3, electronic motor control 14 and motor 2 with its gear unit 5, said electrical unit being located above the spindle channel 46.

A surgeon can grip, hold as well as handle the motor drive installed in a housing 1 by means of his half-closed hand between the row of fingers and the thumb. In this type of construction the motor drive and the dilation catheter 18 can be easily guided and handled with one however also with both hands.

We claim:

1. Motor drive and dilation catheter for reopening of blood vessels, the dilation catheter is insertable through vessels leading to a constriction point and includes a working head for reopening the vessel constriction, wherein the improvement comprises a metal housing shaped for gripping, holding and handling by the half-closed hand of a surgeon between his row of fingers and his thumb, means for sealing said housing in a gas tight manner up to at least 130° C. and 3 bars pressure and said means including a front and a rear bearing package, an electrical battery-driven motor with a motor gearing train mounted in said housing, a hollow spindle open at opposite ends thereof is positioned inn said housing and is supported therein in the front bearing package with a seal and the rear bearing package with a seal, a junction point at one end of the spindle for receiving and holding the dilation catheter means for effecting force transmission from the motor to the spindle, the housing comprises a spindle channel having a front end ad a rear end, the front bearing package is located in the front end of said spindle channel and comprises a front sleeve, a front bearing and an annular support with a front bearing seal located within the front sleeve, the rear bearing package comprises a rear bearing and a rear sleeve, and the front and rear bearing packages are arranged in the spindle channel in a gas-tight manner by seal sleeves, the motor and the motor gearing being round and having substantially the same diameter and are aligned on a longitudinal axis parallel with a spindle axis of the spindle, and intermediate wall being arranged in the housing parallel to the spindle axis and the longitudinal axis and dividing the housing into a spindle channel and a separate compartment for the battery and motor.

2. Motor drive and dilation catheter according to claim 1, wherein the motor can be switched on and off by an adjustment button arranged between the battery and the motor in the separate compartment.

3. Motor drive and dilation catheter according to claim 2, wherein the rpm of the motor is adjustable by an electronic motor control and an adjustment button, arranged between the battery and the motor that operates the motor control.

4. Motor drive and dilation catheter for reopening of blood vessels, the dilation catheter is insertable through vessels leading to a constriction point and includes a working head for reopening the vessel constriction, wherein the improvement comprises a metal housing shaped for gripping, holding and handling by the half-closed hand of a surgeon between his row of fingers and his thumb, means for sealing said housing in a gas tight manner up to at least 130° C. and 3 bars pressure and said means including a front and a rear bearing package, and electrical battery-driven motor with a motor gearing train mounted in said housing, a hollow spindle open at opposite ends thereof is positioned in said housing and is supported therein in the front bearing package with a seal and the rear bearing package with a seal, a junction point at one end of the spindle for receiving and holding the dilation catheter, means for effecting force transmission from the motor to the spindle, the housing comprises a spindle channel having a front end and a rear end, the front bearing package is located in the front end of said spindle channel and comprises a front sleeve, a front bearing and an annular support with a front bearing seal located within the front sleeve, the rear bearing package comprises a rear bearing and a rear sleeve, and the front and rear bearing packages are arranged in the spindle channel in a gas-tight manner by seal sleeves, the motor and the motor gearing being round and having substantially the same diameter and are aligned on a longitudinal axis parallel with a spindle axis of the spindle, the dilation catheter being hollow and passable through an inside lumen of the spindle.

5. Motor drive and dilation catheter according to claim 4, wherein the dilation catheter is inserted at the junction point into a chuck with a union nut and a retaining ring.

6. Motor drive and dilation catheter according to claim 4, wherein said force transmission means comprises a toothed belt for positively transmitting force from a gear wheel fastened to the motor to a toothed sleeve fastened to the spindle.

7. Motor drive and dilation catheter according to claim 4, wherein said force transmission means comprises a V-belt for positively transmitting force from a V-belt pulley fastened to the motor to a V-belt sleeve fastened to the spindle.

8. Motor drive and dilation catheter according to claim 4, wherein the front and rear bearings are ball bearings.

9. Motor drive and dilation catheter for reopening of blood vessels, the dilation catheter is insertable through vessels leading to a constriction point and includes a working head for reopening the vessel constriction, wherein the improvement comprises a metal housing shaped for gripping, holding and handling by the half-closed hand of a surgeon between his row of fingers and his thumb, means for sealing said housing in a gas tight manner up to at least 130° C. and 3 bars pressure and said means including a front and a rear bearing package, an electrical battery-driven motor with a motor gearing train mounted in said housing, a hollow spindle open at opposite ends thereof is positioned in said housing and is supported therein in the front bearing package with a seal and the rear bearing package with a seal, a junction point at one end of the spindle for receiving and holding the dilation catheter, means for effecting force transmission from the motor to the spindle, the housing comprises a spindle channel having a front end and a rear end, the front bearing package is located in the front end of said spindle channel and comprises a front sleeve, a front bearing and an annular support with a front bearing seal located within the front sleeve, the rear bearing package comprises a rear bearing and a rear sleeve, and the front and rear bearing packages are arranged in the spindle channel in a gas-tight manner by seal sleeves, the spindle being embraced by spindle seals which rest inside the front and rear sleeves.

10. Motor drive and dilation catheter according to claim 9, wherein the spindle seals are formed of silicone.

11. Motor drive and dilation catheter according to claim 9, wherein each of the spindle seals are provided with at least one sealing lip.

12. Motor drive and dilation catheter for reopening of blood vessels, the dilation catheter is insertable through vessels leading to a constriction point and includes a working head for reopening the vessel constriction, wherein the improvement comprises a metal housing shaped for gripping, holding and handling by the half-closed hand of a surgeon between his row of fingers and his thumb, means for sealing said housing in a gas tight manner up to at least 130° C. and 3 bars pressure and said means including a front and a rear bearing package, an electrical battery-driven motor with a motor gearing train mounted in said housing, a hollow spindle open at opposite ends thereof is positioned in said housing and is supported therein in the front bearing package with a seal and the rear bearing package with a seal, a junction point at one end of the spindle for receiving and holding the dilation catheter, means for effecting force transmission from the motor to the spindle, the housing comprises a spindle channel having a front end and a rear end, the front bearing package is located in the front end of said spindle channel and comprises a front sleeve, a front bearing and an annular support with a front bearing seal located within the front sleeve, the rear bearing package comprises a rear bearing and a rear sleeve, and the front and rear bearing packages are arranged in the spindle channel in a gas-tight manner by seal sleeves, the housing comprising a battery compartment for the battery together with the battery compartment cover, a battery compartment seal, a control part seal, a cover seal, a front bearing seal and a sleeve seal being O-rings.

13. Motor drive and dilation catheter for reopening of blood vessels, the dilation catheter is insertable through vessels leading to a constriction point and includes a working head for reopening the vessel constriction, wherein the improvement comprises a metal housing shaped for gripping, holding and handling by the half-closed hand of a surgeon between his row of fingers and his thumb, means for sealing said housing in a gas tight manner up to at least 130° C. and 3 bars pressure and said means including a front and a rear bearing package, an electrical battery-driven motor with a motor gearing train mounted in said housing, a hollow spindle open at opposite ends thereof is positioned in said housing and is supported therein in the front bearing package with a seal and the rear bearing package with a seal, a junction point at one end of the spindle for receiving and holding the dilation catheter, means for effecting force transmission from the motor to the spindle, the housing comprises a spindle channel having a front end and a rear end, the front bearing package is located in the front end of said spindle channel and comprises a front sleeve, a front bearing and an annular support with a front bearing seal located within the front sleeve, the rear bearing package comprises a rear bearing and a rear sleeve, and the front and rear bearing packages are arranged in the spindle channel in a gas-tight manner by seal sleeves, a gearing train cover with a temperature sensor being arranged at the motor gearing train in the housing.

* * * * *